United States Patent
Johnson

(10) Patent No.: US 8,138,228 B2
(45) Date of Patent: *Mar. 20, 2012

(54) LIQUID KELP FORMULATION WITH OR WITHOUT ENHANCED SHELF LIFE, AND METHOD OF MAKING

(75) Inventor: Louis B. Johnson, Troy, AL (US)

(73) Assignee: Accelegrow Technologies, Inc., West Point, GA (US)

(*) Notice: Subject to any disclaimer, the term of this patent is extended or adjusted under 35 U.S.C. 154(b) by 568 days.

This patent is subject to a terminal disclaimer.

(21) Appl. No.: 12/285,542

(22) Filed: Oct. 8, 2008

(65) Prior Publication Data

US 2009/0042729 A1 Feb. 12, 2009

Related U.S. Application Data

(63) Continuation of application No. 11/211,424, filed on Aug. 26, 2005, now abandoned.

(60) Provisional application No. 60/610,202, filed on Sep. 16, 2004.

(51) Int. Cl.
*A01N 33/18* (2006.01)
*A01N 33/24* (2006.01)
*A61K 31/04* (2006.01)
*A61K 9/00* (2006.01)

(52) U.S. Cl. .......... 514/740; 514/970; 424/400

(58) Field of Classification Search .......... 514/740, 514/970; 424/400
See application file for complete search history.

(56) References Cited

U.S. PATENT DOCUMENTS

| 4,383,845 | A * | 5/1983 | Rutherford ............ 71/16 |
| 4,816,568 | A * | 3/1989 | Hamilton et al. ........ 530/399 |
| 5,009,710 | A * | 4/1991 | Bewsey .............. 106/205.9 |
| 6,251,878 | B1 | 6/2001 | Strickland et al. |
| 6,410,498 | B1 | 6/2002 | Smets et al. |
| 6,458,546 | B1 | 10/2002 | Baker |
| 2002/0053229 | A1 | 5/2002 | Varshovi |
| 2005/0123499 | A1* | 6/2005 | Majmudar ............ 424/74 |
| 2005/0234041 | A1 | 10/2005 | Tomazic et al. |
| 2005/0288188 | A1 | 12/2005 | Volgas et al. |
| 2007/0020342 | A1 | 1/2007 | Modak et al. |

OTHER PUBLICATIONS

SeaCrop Soluble Kelp Powder (SeaCrop Liquid Kelp ExtractTM, retrieved on Mar. 27, 2008 via online www.archive.org/web/19990423150329/http://www.noamkelp.com/solpowder.html, dated on Apr. 23, 1999.

* cited by examiner

*Primary Examiner* — Johann Richter
*Assistant Examiner* — Mei-Ping Chui
(74) *Attorney, Agent, or Firm* — Clark & Brody

(57) ABSTRACT

A liquid kelp formulation includes an enzyme inactivating component and a preservative to extend the shelf life of the formulation in terms of growth hormones. The formulation can also include a fertilizing additive, and a surfactant. A system is also provided whereby the kelp is maintained in solid form, and dissolved in water just prior to use. The solid form kelp and/or water can include additives, or additives in separate form, if used, can be added to either the kelp or the kelp solution.

18 Claims, No Drawings

LIQUID KELP FORMULATION WITH OR WITHOUT ENHANCED SHELF LIFE, AND METHOD OF MAKING

This is a continuation of U.S. patent application Ser. No. 11/211,424 filed on Aug. 26, 2005 now abandoned, which claims priority under 35 USC 119(e) based on provisional patent application no. 60/610,202 filed on Sep. 16, 2004, and is incorporated herein by reference.

TECHNICAL FIELD

The present invention relates to a liquid kelp formulation and a method of making, and in particular to a formulation that includes an enzyme inactivating component and preservative.

BACKGROUND ART

Kelp, commonly referred to as seaweed, grows along coastlines around the world and is botanically classified as algae. The use of liquid kelp as a growth stimulant is well known in the agricultural industry. This seaplant is rich in micronutrients and natural growth hormones, including cytokinins, auxins and gibberellins, which stimulate cell division and larger root systems. Kelp extracts can be applied as a foliar spray on plants and the like, or on soil for later contact and absorption by root structures. An extract applied to land plants is known to accelerate growth, increase fruiting and flowering, intensify color, and provide resistance to disease, insects, drought, and frost. Many commercial liquid formulations of kelp are available for use in the agricultural industry and can be found in various retail and wholesale outlets, as well as through the internet. These kelp formulations are basically an extract of kelp diluted with water, and may contain other components as the manufacturer of the formula may see fit. Examples of formulations include those sold at the Gardens Alive website www.gardensalive.com, Sea Crop Liquid Kelp Extract (to be diluted in water), and the like.

It is also known to use kelp in tablet or capsule form to treat different health problems. One problem with present day liquid kelp materials is the short shelf life of the formulation. When the kelp is combined with water and other components, bacteria or other impurities present in the water or other additives break down the growth hormones found in the kelp, thus rendering them ineffective over time.

Thus, a need exists to provide improved kelp formulations, including those that have extended shelf lives. The present invention responds to this need by providing a liquid kelp formulation that has an increased shelf life.

SUMMARY OF THE INVENTION

One object of the present invention is an improved liquid kelp formulation.

Another object of the invention is a method of making the liquid formulation.

Yet another object is a system of providing kelp for agricultural purposes, but without subjecting the kelp to prolonged exposure to water and/or other additives.

Other objects and advantages will become apparent as a description thereof proceeds.

In satisfaction of the foregoing objects and advantages, the invention is an improvement in liquid kelp formulations by the presence of an effective amount of an enzyme inactivating component selected from the group consisting of sarcosine, manganese chloride, and sodium dodecyl sulfate to reduce the degradation of growth hormones in the liquid kelp formulation. A preservative is also included, the preservative amount effective to retard growth of bacteria, fungi, and/or mold in the liquid kelp formulation. The enzyme inactivating component preferably ranges from zero and up to 5.0% by weight of the formulation, more preferably between 0.25% and 3.0%, and most preferably between 0.5 to 1.5%. A preferred enzyme inactivating component is sarcosine.

The preservative is preferably a food grade preservative and/or the preservative is in a range of from 0.10 to 1% by weight, more preferably between 0.15% and 0.5%, and most preferably around 0.2-0.3%. The preservative is preferably one of methyl paraben, propyl paraben, and diazolidinyl urea.

The formulation can also include an effective amount of a surfactant for wetting purposes, preferably a nonionic surfactant such as an alcohol ethoxylate. The alcohol ethoxylate preferably has 9 or more moles of ethoxylation.

The formulation can also include a source of nitrogen, phosphorous, or potassium, and if nitrogen is used, it is preferred to use a compound containing ammonia.

The invention entails the method of using the formulation wherein the liquid kelp formulation is applied to plant, for example, by direct application to the plants themselves, including to the foliage and/or roots of the plants, and to the soil in the vicinity of the plants.

Another aspect of the invention entails improvements in the method of applying a liquid kelp formulation to plants. In this aspect, the kelp is provided into a solid form, made into a solution, and immediately applied to plants or soil. This method can be modified by including the enzyme inactivating component and/or preservative discussed above. The enzyme inactivating component and/or preservative can be present as part of either the solid kelp or the water prior to the adding step. In another alternative, the enzyme inactivating component and/or preservative could be maintained as separate components and added either individually or together to either the water or a water-kelp solution.

DESCRIPTION OF THE PREFERRED EMBODIMENTS

The present invention is an improvement over the kelp formulations found in the prior art. By practicing the invention, the breakdown of the growth hormones found in kelp is slowed or eliminated as a result of additives combined with the kelp or the manner in which the kelp is combined with water and additives.

The liquid kelp formulation or system of the invention can be applied to plants or any vegetation that would require a boost in growth or benefit from other effects attributable to kelp. The term "plants" is intended to encompass any and all vegetation in this regard that would benefit from application of kelp. Examples includes vegetables, flowers, shrubs, trees, grasses, fruits, vines, etc., and their roots in the event that the formulation is used as a root dip or applied to soil to improve root structure.

In one embodiment of the invention, an additive-containing kelp formulation is made that has extended shelf life, and can then be used at a later time to stimulate growth in plants and the like.

In another embodiment, a system is provided that produces an aqueous liquid formulation, with or without various additives. As part of this system, the kelp is maintained separately from liquid formulation until the formulation as made is to be applied in a given manner. The kelp, in virtually any solid form, can be added to the aqueous liquid formulation. The formulation can contain additives when combined with the kelp, can be additive free, or can have the additives added after kelp addition. For example, the solid form of the kelp could be a capsule, a pellet, granule, tablet, meal, or other solid form. The additives can be those employed with the liquid formulation of the invention, or other known additives that are commonly found in kelp formulations.

Turning to the liquid kelp formulation aspect of the invention, one additive is an enzyme inactivating component such as sarcosine, manganese chloride, sodium dodecyl sulfate, sodium lauryl sarcosinate, grape seed oil, pine bark extract, grape leaf, black currant, passion flower, and *chlorella vulgaris* with sarcosine being a preferred enzyme inactivating component. An effective amount is employed in the liquid kelp formulation such that the growth hormones therein do not break down as fast over time as they would without the inactivating additive. A more preferred amount is up to 5.0% by weight of the total formulation, with more preferred ranges between 0.25 and 3.0%, and most preferably between 0.5 to 1.5%. Enzyme inactivating compounds are disclosed in U.S. Pat. No. 6,458,546 to Baker et al. (Baker), which is herein incorporated in its entirety by reference. It should be noted that the Baker patent references SARKOSYL as one of the enzyme inactivating ingredients. SARKOSYL is actually a trademark, and the proper chemical reference is sarcosine, as noted in Hawley's The Condensed Chemical Dictionary, Eighth Edition, pp. 774 and 775. The chemical name for sarcosine is methyl glycocoll aminoacetic acid. The Baker patent is not relevant to the present invention and is concerned with the preservation of DNA in samples, and discloses the addition of the enzyme inactivating components in combination with a divalent metal chelator such as EDTA, EGTA, and BAPTA, and at least one chelator enhancing component such as lithium chloride, guanidine, sodium salicylate, sodium perchlorate, and sodium thiocyanate, each in specified amounts. It is contemplated that the chelator and chelator-enhancing component of Baker could be employed with the effective amount of the enzyme inactivating components that is utilized in the present invention if so desired, and in the amounts taught by Baker.

Another additive for the liquid kelp formulation is a preservative in an amount effective to preserve the formulation and resist bacterial, fungi, and/or mold growth. Preferred ranges include from 0.10 to 1% by weight, more preferred ranges include 0.15% to 0.5% with a target of around 0.2-0.3%. Virtually any known preservative can be employed in the formulation, with examples including those using propyl paraben, methyl paraben, and diazolidinyl urea, e.g., Germaben II. Another specific preservative that can be used is Dantoguard® manufactured by Lonza, see www.Lonza.com. Dantoguard® Plus is another preservative adaptable for use in the invention, this particular preservative more adapted for battling fungi and bacteria.

Since the kelp could be sprayed on food bearing plants, it is important to ensure that the additives are food safe. In this regard, if the liquid kelp is intended to be sprayed on plants or other vegetation or come into contact with any vegetation that may be eaten or bear fruit, the preservative should be a food grade preservative such as the methyl or propyl parabens mentioned above.

If so desired, the kelp formulation could be enhanced with additional fertilizing additives or agents that provide nitrogen, phosphorous, or potassium. One example would be an amount of ammonia to provide additional nitrogen. The amount should be sufficient to have an effect on the treated plants, with a preferred amount being up to about 2.0% by weight of the formulation, and more preferably up to 1.0% by weight.

One example of a preferred formulation is as follows:

| Component | Percentage by weight | 55 gallons (in lbs. except for water) | 5 gallons (in lbs.) |
|---|---|---|---|
| Powdered kelp | 5.0 | 23 | 2.0 |
| Nipasol-m-sodium[1] | 0.3 | 1.4 | 0.1 |
| Ammonia[2] | 0.5% | 2.3 | 0.2 |
| Sarcosine | 1.0 | 4.6 | 0.4 |
| Water | 93.2 | 51 gallons | 37.2 |

[1]Nipasol-m-sodium is a propyl paraben preservative.
[2]Ammonia is added as an additional fertilizer boost.

In formulating the liquid kelp, it is preferred to dissolve the preservative into the water first while taking the necessary precautions to avoid inhaling any of the preservative, and then add the remaining components, although the components could be added in any order if so desired.

The liquid kelp formulation can be made in a concentrated form which would be diluted by the end user, or in a ready to use concentration as exemplified by the table above, with either of these modes of delivery well known in the art. When making a concentrate, the weight percentages of the various additives would be adjusted so that when the concentrate is diluted, the percentages still fall within the ranges given above for the broad and more preferred embodiments of the invention.

The manner of application of the liquid kelp formulation can be any type known in the art. For example, the formulation can be used as a foliar spray, or for dipping plant roots, or applied directly to soil so that the formulation can interact with roots of the plants in the soil.

It should also be understood that the formulation can include one or more surfactants for wetting if so desired. When using a surfactant, virtually any surfactant that imparts wetting to the formulation can be used. A preferred class of surfactants includes nonionic types such as alcohol ethoxylates, with preferred moles of ethoxylation being about 9 or more.

The kelp can be obtained from any commercial source of kelp for use in the invention, either in making the liquid kelp formulation or a solid form for later dissolution and use.

As mentioned above, another aspect of the invention is a system entailing making of a liquid kelp formulation by providing a solid form of kelp and dissolving it in water. The water can contain other additives as desired. Alternatively, the kelp in solid form could contain the additives, as desired. The additives can be those known in the art such as fertilizing additives, or the additives noted above.

In an alternate mode of this aspect of the invention, the additives could be separate from the water and solid kelp and added to the water, either before or after dissolving the kelp.

This system of the invention is advantageous in that the kelp is kept separate from the water and its impurities until it is desired to apply the kelp to a given plant or area. Thus, a potent kelp liquid is provided that does not suffer from potency loss like liquid kelps that have been stored over time do. The form of the solid kelp can be any type, e.g., tablet, pill, capsule, powder, granule, pellet, cake, or the like. The form of the additives can also be any type, liquid or solid. As noted above, the additives can be any type typically found in known kelp formulations or they can include those mentioned above in terms of the enzyme inactivating component, preservative, and/or surfactant and fertilizer. It is anticipated that the enzyme inactivating component may be optional in this mode of the invention since the kelp would be used immediately after forming the liquid, and the breakdown of growth hormones would not be the significant problem that it is with prior art kelp liquids. The preservative may also be optional, but could be added to the solid kelp to preserve its shelf life.

As such an invention has been disclosed in terms of preferred embodiments thereof, which fulfills each and every one of the objects of the invention as set forth above, and provides a liquid kelp formulation, methods of use, methods of making, and a system of making a kelp formulation that minimize kelp contact with water.

Of course, various changes, modifications and alterations from the teachings of the present invention may be contemplated by those skilled in the art without departing from the intended spirit and scope thereof. It is intended that the present invention only be limited by the terms of the appended claims.

I claim:

1. In a liquid kelp formulation having kelp as a major active ingredient, the improvement comprising an effective amount of sarcosine as an enzyme inactivating component to reduce the degradation of growth hormones in the liquid kelp formulation, and a preservative in an amount effective to retard growth of bacteria, fungi, and/or mold in the liquid kelp formulation.

2. The formulation of claim 1, wherein the enzyme inactivating component ranges up to 5.0% by weight of the formulation.

3. The formulation of claim 2, wherein the enzyme inactivating component ranges between 0.25 and 3.0% by weight of the formulation.

4. The formulation of claim 1, wherein the preservative is a food grade preservative.

5. The formulation of claim 4, wherein the preservative is in the range of from 0.10 to 1.0% by weight of the formulation.

6. The formulation of claim 5, wherein the preservative is in the range of from 0.15 to 0.5% by weight of the formulation.

7. The formulation of claim 1, wherein the preservative is one of methyl paraben, propyl paraben and diazolidinyl urea.

8. The formulation of claim 1, further comprising an effective amount of a surfactant for wetting purposes.

9. The formulation of claim 8, wherein the surfactant is an alcohol ethoxylate.

10. The formulation of claim 9, wherein the alcohol ethoxylate has 9 or more moles of ethoxylation.

11. The formulation of claim 1, further comprising a plant fertilizing agent comprising nitrogen, phosphorous, or potassium.

12. The formulation of claim 11, comprising ammonia as the nitrogen source.

13. A method for plant growth stimulation comprising applying an liquid kelp formulation to plants, wherein the formulation comprises an amount of kelp, an effective amount of sarcosine as an enzyme inactivating component to reduce the degradation of growth hormones in the kelp formulation, and a preservative in an amount effective to retard growth of bacteria, fungi, or mold in the liquid kelp formulation.

14. The method of claim 13, wherein the formulation is applied directly to the plants or applied to the plants indirectly via application to soil.

15. A method for plant growth stimulation comprising:
providing a solid form of kelp and dissolving it in water to form a liquid kelp solution, and immediately applying it to plants,
wherein the liquid kelp solution includes an addition of sarcosine as an enzyme inactivating component in an amount effective to reduce the degradation of growth hormones in the liquid kelp formulation, and a preservative in an amount effective to retard growth of bacteria, fungi, or mold in the liquid kelp formulation.

16. The formulation of claim 3, wherein the enzyme inactivating component ranges between 0.5 and 1.5% by weight of the formulation.

17. The formulation of claim 6, wherein the preservative is in the range of from around 0.2 to 0.3% by weight of the formulation.

18. The method of claim 15, wherein the amount of kelp used in the adding step produces a liquid kelp solution having kelp as its major active ingredient.

* * * * *